(12) United States Patent
Freelander (10) Patent No.: US 11,627,758 B2
(45) Date of Patent: Apr. 18, 2023

(54) BIODEGRADABLE WRAPPING FOR CARTRIDGES

(71) Applicant: Freelander Innovations USA, LLC, Springfield, MO (US)

(72) Inventor: Michael Freelander, Springfield, MO (US)

(73) Assignee: Freelander Innovations USA, LLC, Springfield, MO (US)

( * ) Notice: Subject to any disclaimer, the term of this patent is extended or adjusted under 35 U.S.C. 154(b) by 6 days.

(21) Appl. No.: 16/314,547

(22) PCT Filed: Jul. 12, 2018

(86) PCT No.: PCT/US2018/041797
§ 371 (c)(1),
(2) Date: Dec. 31, 2018

(87) PCT Pub. No.: WO2019/018196
PCT Pub. Date: Jan. 24, 2019

(65) Prior Publication Data
US 2021/0220580 A1 Jul. 22, 2021

Related U.S. Application Data

(60) Provisional application No. 62/497,296, filed on Jul. 17, 2017.

(51) Int. Cl.
*A24D 1/18* (2006.01)
*A24F 40/20* (2020.01)
(Continued)

(52) U.S. Cl.
CPC ............. *A24D 1/18* (2013.01); *A24F 40/42* (2020.01); *A61M 15/06* (2013.01); *A24F 40/20* (2020.01);
(Continued)

(58) Field of Classification Search
CPC .......... A24F 40/20; A24F 40/42; A24D 1/18; A61M 15/06; A61M 2205/3368;
(Continued)

(56) References Cited

U.S. PATENT DOCUMENTS 1,185,651 A * 6/1916 Name not available ................... A24F 23/02 206/260
2,613,673 A 10/1952 Sartoretto et al.
(Continued)

FOREIGN PATENT DOCUMENTS

EP 1849712 A1 10/2007
EP 2653046 A1 10/2013
(Continued)

OTHER PUBLICATIONS

European Search Report issued for European Application No. 18834727.2 dated May 17, 2021, 8 pages.

*Primary Examiner* — Hae Moon Hyeon
*Assistant Examiner* — Thang H Nguyen
(74) *Attorney, Agent, or Firm* — Husch Blackwell LLP (57) ABSTRACT

An improved cartridge for containing an inhalable substance. The cartridge may comprise a wrapping or exterior material having the same or similar combustion properties as the inhalable substance contained within the cartridge. The cartridge may be placed into a vaporizer or similar device where the inhalable substrate is vaporized to generate a gaseous version of the inhalable substance, such as tobacco vapor, marijuana vapor, or atomized medicine without burning of or contamination by the wrapping or exterior material.

19 Claims, 7 Drawing Sheets

(51) Int. Cl.
*A24F 40/42* (2020.01)
*A61M 15/06* (2006.01)

(52) U.S. Cl.
CPC .............. *A61M 2205/3368* (2013.01); *A61M 2205/582* (2013.01); *A61M 2205/583* (2013.01); *A61M 2205/8206* (2013.01); *A61M 2209/06* (2013.01)

(58) Field of Classification Search
CPC ...... A61M 2205/582; A61M 2205/583; A61M 2205/8206; A61M 2209/06
See application file for complete search history.

(56) References Cited

U.S. PATENT DOCUMENTS

| | | | |
|---|---|---|---|
| 2,799,611 | A | 7/1957 | Dreisbach |
| 5,388,594 | A | 2/1995 | Counts et al. |
| 6,713,175 | B1 | 3/2004 | Terada et al. |
| 6,959,712 | B2 | 11/2005 | Bereman et al. |
| 8,056,566 | B2 | 11/2011 | Kang et al. |
| 8,251,072 | B1 | 8/2012 | Zepp |
| 8,863,750 | B2 | 10/2014 | Boll et al. |
| 8,905,037 | B2 | 12/2014 | Lipowicz et al. |
| 9,351,521 | B2 | 5/2016 | Drezen et al. |
| 10,925,317 | B2 * | 2/2021 | Smith ..................... A24F 40/30 |
| 2003/0217757 | A1 | 11/2003 | Edelmann |
| 2004/0055613 | A1 | 3/2004 | Horian |
| 2004/0134631 | A1 | 7/2004 | Crooks et al. |
| 2008/0044110 | A1* | 2/2008 | Garger ................... B65D 31/10 383/5 |
| 2009/0229620 | A1 | 9/2009 | De Castro Neto |
| 2011/0180432 | A1 | 7/2011 | Blick et al. |
| 2012/0318286 | A1 | 12/2012 | Lisauskas et al. |
| 2014/0137879 | A1* | 5/2014 | Sebastian ............... A24D 3/068 131/332 |
| 2014/0224268 | A1* | 8/2014 | Ryter ..................... A24D 3/045 493/39 |
| 2015/0374030 | A1* | 12/2015 | Lisauskas ................ A24D 3/10 162/146 |
| 2016/0296464 | A1* | 10/2016 | Lindsay ................ A61K 9/006 |
| 2016/0324216 | A1 | 11/2016 | Li et al. |
| 2016/0331913 | A1 | 11/2016 | Bourque |
| 2016/0360783 | A1 | 12/2016 | Patel et al. |
| 2017/0042217 | A1 | 2/2017 | Fernandez et al. |
| 2017/0112188 | A1* | 4/2017 | Ostrander ............... A24D 1/02 |
| 2017/0157106 | A1* | 6/2017 | Rogers .............. B65D 85/1081 |
| 2017/0181468 | A1* | 6/2017 | Bowen .................... A24F 42/10 |
| 2018/0057220 | A1* | 3/2018 | Branson ............. B65D 33/2541 |
| 2019/0254346 | A1* | 8/2019 | Hepworth ............. A61M 15/06 |
| 2020/0164165 | A1* | 5/2020 | Lord ..................... A61M 15/06 |

FOREIGN PATENT DOCUMENTS

| | | | | |
|---|---|---|---|---|
| GB | | 1211247 A | 11/1970 | |
| GB | | 2466204 A | 6/2010 | |
| WO | WO-2007084587 A2 * | | 7/2007 | .............. A23G 3/56 |
| WO | WO-2016171997 A2 * | | 10/2016 | |
| WO | | 2017089611 A1 | 6/2017 | |

\* cited by examiner

BIODEGRADABLE WRAPPING FOR CARTRIDGES

CROSS-REFERENCE TO RELATED APPLICATIONS

This application claims priority to U.S. Provisional Application 62/497,296, filed on Jul. 17, 2017 and titled "BIODEGRADABLE WRAPPING FOR CARTRIDGES". U.S. Application No. 62/497,296 is hereby incorporated by reference. This application also claims priority to PCT Application No. PCT/US18/41797, filed on Jul. 12, 2018 and titled "BIODEGRADABLE WRAPPING FOR CARTRIDGES". PCT Application No. PCT/US18/41797 is also hereby incorporated by reference.

FIELD

The present invention relates generally to packaging of material for vaporizers and inhalers.

BACKGROUND

Inhalers and vaporizers are conventionally used for medicinal and recreational purposes to deliver an inhalable substance in a gaseous form to a user. Vaporizers have been used recreationally with the use of recreational substances such as tobacco, hookah, and cannabis. Meanwhile, rescue inhalers have been used by people having asthma or other medical uses. Furthermore, some medicine may be delivered by an inhaler for some respiratory diseases.

Generally, users of vaporizers, hookahs, electronic hookahs, and so-called "e-cigarettes" insert a loose form of an inhalable substance into a chamber of the corresponding device. However, loose packing of the inhalable substance requires portioning out the inhalable substance and sometimes grinding or packing the inhalable substance prior to insertion into the corresponding device. These actions can be frustrating for users looking to enjoy or benefit from the inhaled substance. Alternatively, some existing solutions prepackage the inhalable substance with a conventional wrapper. However, the conventional wrapper can give off toxic or unpleasant chemicals that modify the experience of consuming the inhalable substance. Thus, there is a need in the art for improved inhalable substance wrapping methods.

DETAILED DESCRIPTION

While this invention is susceptible of an embodiment in many different forms, there are shown in the drawings and will be described herein in detail specific embodiments thereof with the understanding that the present disclosure is to be considered as an exemplification of the principles of the invention. It is not intended to limit the invention to the specific illustrated embodiments.

Embodiments disclosed herein include an improved wrapper for prepackaging an inhalable substance for use in a vaporizer or similar device. The wrapper may have the same or similar combustion properties to the inhalable substance allowing the entirety of the wrapped cartridge to be placed into a chamber of a vaporizer where the inhalable substance and the wrapping is vaporized to generate a gaseous version of the inhalable substance, such as tobacco vapor, marijuana vapor, atomized medicine, or other substances capable of being vaporized without burning of or contamination by the wrapper. In some embodiments, the inhalable substance can comprise a blend of herbal materials (e.g. a blend of tobacco materials, a blend of marijuana materials, or a blend of tobacco and marijuana materials).

Figure 1:
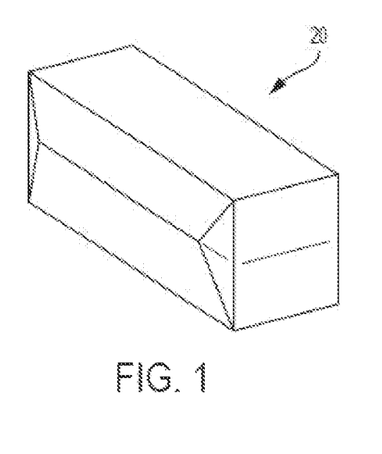
FIG. 1 illustrates a prepackaged cartridge of an inhalable substance according to an exemplary embodiment.
Figure 2:
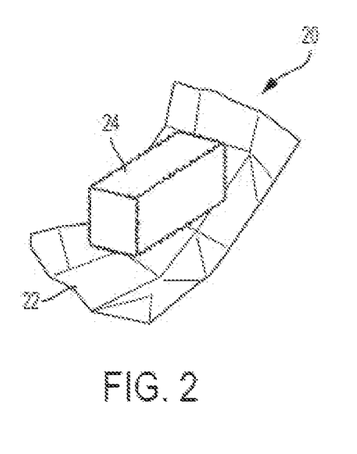
FIG. 2 illustrates an internal view of a prepackaged cartridge of an inhalable substance according to an exemplary embodiment.
Figure 3:
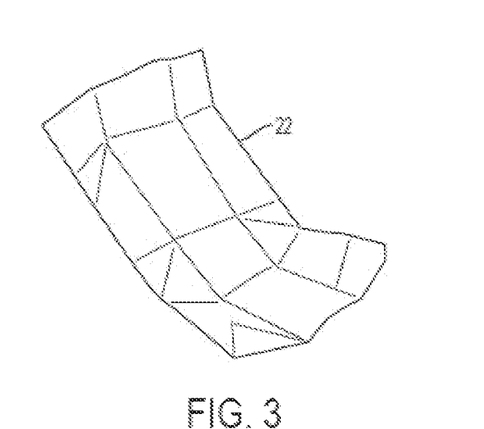
FIG. 3 illustrates a wrapper of a prepackaged cartridge for an inhalable substance according to an exemplary embodiment.

Referring now to FIGS. 1 to 4, a preferred embodiment of a prepackaged cartridge 20 of an inhalable substance is shown. As shown in FIG. 2, a prepackaged cartridge 20 may include a wrapper 22 and a compressed form 24 of the inhalable substance. Wrapper 22 may enclose compressed form 24 to maintain a compact shape and to allow for easy placement of cartridge 20 into a chamber of a vaporizer or similar device. In one embodiment, wrapper 22 may comprise a biodegradable substance (e.g. hemp paper, hemp cloth, cannabis paper, cannabis cloth, leaf paper, leaf cloth, wax paper, or other substances) that has the same or similar combustion properties (e.g. temperature) as the inhalable substance 24. In some embodiments, wax paper can be applicable for filling pipes or other devices that will not need heat transfer. Because the wrapper 22 may have the same or similar combustion properties as the inhalable substance, the entire cartridge 20 may be placed into a vaporizer for vaporization of the inhalable substance without risking burning of the wrapper 22, which if allowed to burn may be toxic or may distort the taste of the inhalable substance. In some embodiments, the prepackaged cartridge 20 may not be sized to easily fit into a small or oddly shaped chamber. The wrapper 22 may be configured to maintain enclosure of compact form 24 while a user compresses or manipulates the prepackaged cartridge 20 so as to fit the prepackaged cartridge 20 into the small or oddly shaped chamber.

According to an exemplary embodiment, the prepackaged cartridge 20 can include medicated measurements varying in size from 0.05 grams to 0.10 grams, 0.2 grams, 0.25 grams, 0.3 grams, 0.4 grams, 0.5 grams, 0.6 grams, ¼ oz., ½ oz., 1 lb., and 1 kilogram.

Figure 4:
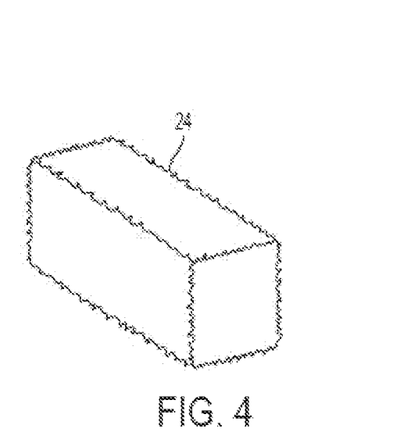
FIG. 4 illustrates a compressed and unwrapped amount of an inhalable substance for a prepackaged cartridge according to an exemplary embodiment.

In one embodiment, the compressed form 24 may be packed into a three-dimensional form (e.g. preferably rectangular) as shown in FIG. 4. The inhalable substance may be packed such that sufficient airflow may be achieved when vaporizing the inhalable substance into a gaseous version.

Figure 5:
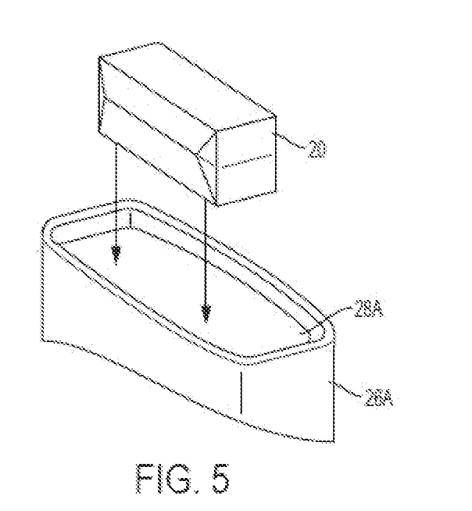
FIG. 5 illustrates a prepackaged cartridge of an inhalable substance being inserted into a vaporizer chamber according to an exemplary embodiment.
Figure 6:
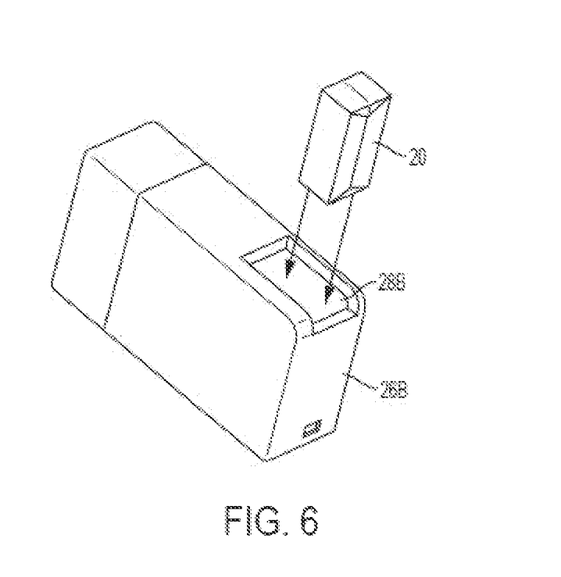
FIG. 6 illustrates a prepackaged cartridge of an inhalable substance being inserted into a vaporizer chamber according to an exemplary embodiment.

Referring now to FIGS. 5 and 6, example embodiments of vaporizer devices 26A and 26B for receiving prepackaged cartridge 20 are shown. Vaporizer devices 26A and 26B may comprise respective chambers 28A and 28B for receiving the prepackaged cartridge 20. In one embodiment, the compact form 24 (see FIG. 4) may be specifically sized to fit into the cavities 28A or 28B. Once the prepackaged cartridge 20 is inserted into the chamber 28A or 28B, the chamber 28A or 28B may be sealed. Following exhaustion of the inhalable substance, the chamber 28A or 28B may be unsealed and the scrap or remnants of prepackaged cartridge 20 may be removed. In one embodiment, the scrap may be approximately 50% lower in mass than the unvaporized prepackaged cartridge 20.

The vaporizer devices 26A and 26B can also comprise a heating element (not shown) that vaporizes the inhalable substance within the prepackaged cartridge 20. The heating element can include a heating element of any type, include a coil, a convection heater, a conduction heater, laser, or a flame. The heat generated by the heating element can vaporize the inhalable substance through the wrapper 22.

In some embodiments, prepackaged cartridge 20 may be placed into a device, such as a hookah, an electronic hookah, and an e-cigarette. In other embodiments, prepackaged cartridge 20 may be placed into a combustion device that burns the inhalable substance along with the wrapper 22 to simulate the experience of smoking the inhalable substance. In this embodiment, wrapper 22 may comprise a paper material or alternative materials similar to paper.

Figure 7:
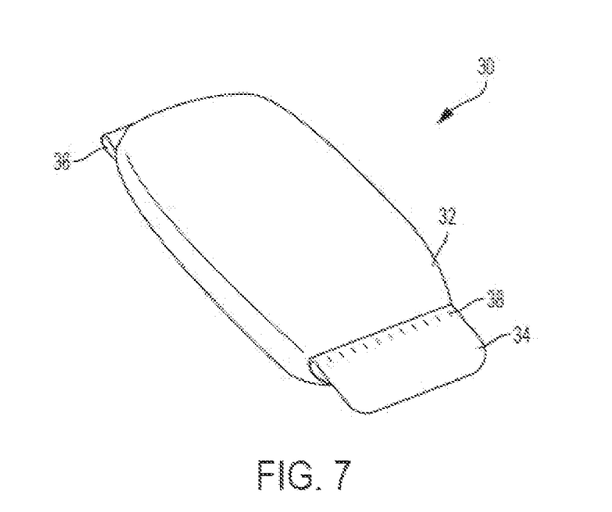
FIG. 7 illustrates a prepackaged cartridge of an inhalable substance according to an exemplary embodiment.

Referring now to FIG. 7, an example embodiment of a prepackaged cartridge 30 of an inhalable substance is shown. Prepackaged cartridge 30 may include a bag 32, a first tab 34, and a second tap 36. Bag 32 contains the inhalable substance and may be sealed off by first and second tabs 34 and 36. In an exemplary embodiment, the inhalable substance may be packed such that sufficient airflow may be achieved when vaporizing the inhalable substance into a gaseous version. The first and second tabs 34 and 36 may be joined to the bag 32 by a sewn seem 62 that seals the inhalable substance within bag 32. In some embodiments a different combination of tabs or structures (e.g. one tab, more than two tabs, sewing closed the bag, etc.) may be used to seal the bag 32.

In one embodiment, the bag 32 may be made of a biodegradable substance (e.g. hemp paper, hemp cloth, cannabis paper, cannabis cloth, leaf paper, leaf cloth, etc.) that has the same or similar combustion properties (e.g. temperature) as the inhalable substance within the bag 32. Because the bag 32 may have the same or similar combustion properties as the inhalable substance, the entire prepackaged cartridge 30 may be placed into a vaporizer, and vaporization of the inhalable substance may be achieved without risking burning of bag 32, which if allowed to burn may be toxic or may distort the taste of the inhalable substance. In some embodiments, the bag 32 may not be sized to easily fit into a small or oddly shaped chamber. The bag 32 may be configured to contain the inhalable substance while a user compresses or manipulates the bag 32 so as to fit the bag into the small or oddly shaped chamber.

Figure 8:
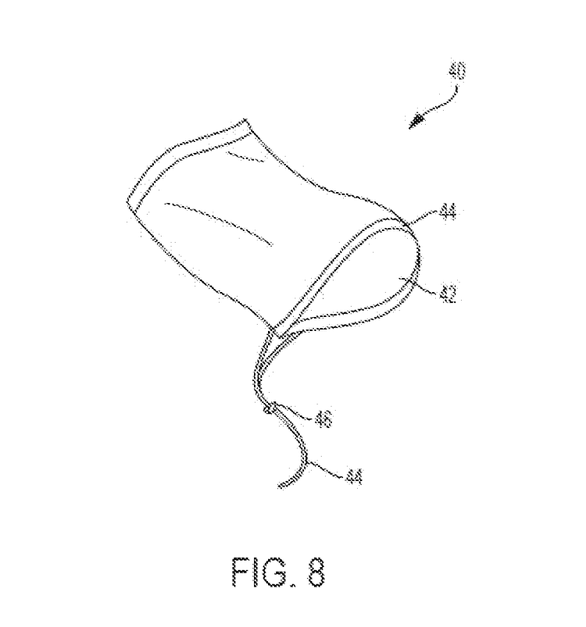
FIG. 8 illustrates a user fillable cartridge for an inhalable substance according to an exemplary embodiment.

Referring now to FIG. 8, an example embodiment of a user fillable cartridge 40 for an inhalable substance is shown. User fillable cartridge 40 may include an opening 42, a closure mechanism 44, and a fastener 46. User fillable cartridge 40 may be filled with an inhalable substance through opening 42 and sealed by closure mechanism 44 and fastener 46. In one embodiment, closure mechanism 44 may be a drawstring threaded into the body of the user fillable cartridge 40 near the opening 42. The closure mechanism 44 may be configured to cinch opening 42 closed and be held closed by fastener 46. In one embodiment, the cinch opening 42 may be a string or thread onto the closure mechanism 44. The user fillable cartridge 40 may be configured to allow a user to pre-portion bulk amounts of an inhalable product into a single serving amount for placement into a vaporizer or similar device.

In one embodiment, the user fillable cartridge 40 may be made of a biodegradable substance (e.g. hemp paper, hemp cloth, cannabis paper, cannabis cloth, leaf paper, leaf cloth, etc.) that has a similar or the same combustion properties (e.g. temperature) as the inhalable substance it is containing. The user fillable cartridge 40 having the same or similar combustion properties as the inhalable substance allows placement of the entire user fillable cartridge 40 into a vaporizer and vaporization of any inhalable substance placed inside without risking burning of the user fillable cartridge 40, which if allowed to burn may be toxic or may distort the taste of the inhalable substance. In some embodiments, the user fillable cartridge 40 may not be sized to easily fit into a small or oddly shaped chamber. The user fillable cartridge 40 may be configured to contain the inhalable substance while a user compresses or manipulates the user fillable cartridge 40 so as to fit the bag into the small or oddly shaped chamber.

Figure 9:
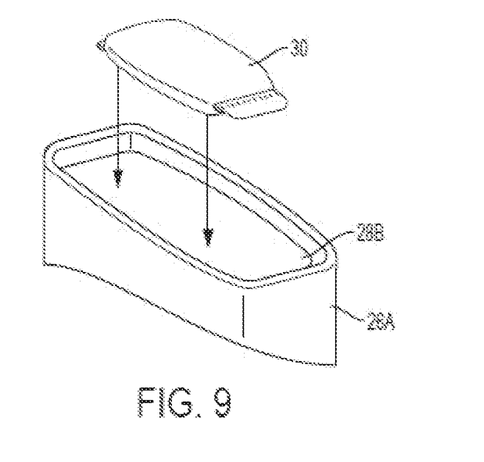
FIG. 9 illustrates a prepackaged cartridge of an inhalable substance being inserted into a vaporizer chamber according to an exemplary embodiment.
Figure 10:
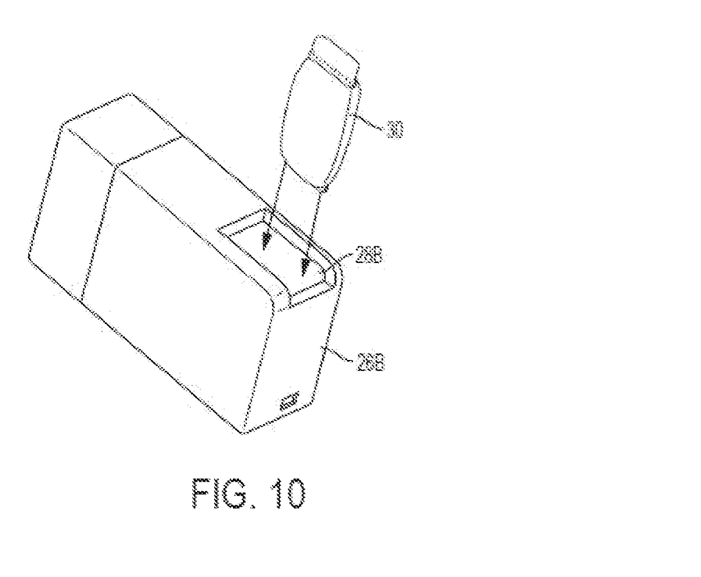
FIG. 10 illustrates a prepackaged cartridge of an inhalable substance being inserted into a vaporizer chamber according to an exemplary embodiment.

Referring now to FIGS. 9 and 10, example embodiments of vaporizer devices 26A and 26B receiving prepackaged cartridge 30 are shown. In one embodiment, prepackaged cartridge 30 may be specifically sized to fit into a chamber 28A or 28B. Once the prepackaged cartridge 30 is inserted into the chamber 28A or 28B, the chamber 28A or 28B may be sealed and the vaporization process of the inhalable substance may begin. Following exhaustion of the inhalable substance, chambers 28A or 28B may be unsealed, and scrap or remnants of the prepackaged cartridge 30 may be removed. In one embodiment, the scrap may be approximately 50% lower in mass than the original prepackaged cartridge 30.

In some embodiments, the prepackaged cartridge 30 may be placed into a device, such as a hookah, an electronic hookah, and an e-cigarette. In other embodiments, the prepackaged cartridge 30 may be placed into a combustions device that burns the inhalable substance along with the prepackaged cartridge 30 to simulate the experience of smoking the inhalable substance. In the burning embodiment, prepackaged cartridge 30 may comprise a paper material.

Some embodiments may be directed to a method for packing an inhalable substance into single portion cartridges for using in a vaporizer or other device. In some embodiments, such a method may include compressing a select amount of an inhaled substance into a three-dimensional shape (e.g. rectangular). The three-dimensional shape may be placed on a wrapping material having the same or similar combustion properties as the inhalable substance. In one embodiment, the wrapping material may be precut to a size for wrapping a single three-dimensional shape. In another embodiment, multiple three-dimensional shapes are placed onto a large sheet of the wrapping material and the wrapping material is then cut to a size for wrapping each single three-dimensional shape. The wrapping material may be folded around the three-dimensional shape such that it encloses and seals the inhalable substance. The cartridge comprising the wrapping material and the three-dimensional shape may be placed into a vaporizer or similar device for consumption of the inhalable substance.

Vaporizer devices such as 26A and 26B (see FIGS. 5, 6, 9, and 10) may include external controls for setting and changing programs dictating heat applied to any of prepackaged cartridge 20, prepackaged cartridge 30, or user packed cartridge 64.

Figure 13A:
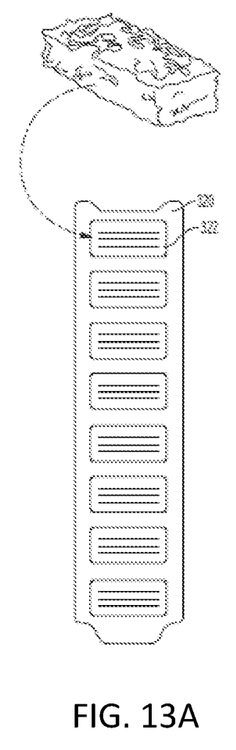
FIGS. 13A and 13B illustrate a prepackaged cartridge of an inhalable substance in a strip according to an exemplary embodiment.

Referring to FIG. 13A, replaceable strip 320 may comprise a plurality of cartridges 322, and each cartridge comprises inhalable substance. The replaceable strip 320 may comprise a substrate on which either the cartridges 322 or a continuous band 324 (FIG. 13B) are disposed.

Figure 13B:
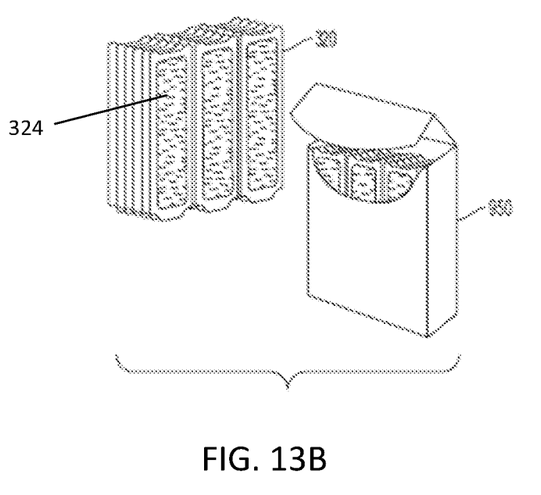

According to an exemplary embodiment, the replaceable strip 320 may include any number of cartridges 322, although FIG. 13A illustrates eight cartridges. Each cartridge 322 may hold a vacuum-packed serving of the inhalable substance, such as tobacco or cannabis. According to an exemplary embodiment, the replaceable strip 320 may be covered by the wrapper 22, which may have the same or similar combustion properties as the inhalable substance within each cartridge 322. The inhalable substance may be centered and held in place by its packing material (e.g. hemp wrapping paper) or held in place within the replaceable strip 320 by one or more prongs or tabs. The cartridges 322 may hold the inhalable substance in ground form, leaf form, or gel form, but the cartridges 322 is not limited to only these forms. In some embodiments, the cartridges 322 can be similar in structure to the cartridges 20 described above. FIG. 13B illustrates that a plurality of replaceable strips 320 may be contained within a container 950 and sold in packs.

Figure 11:
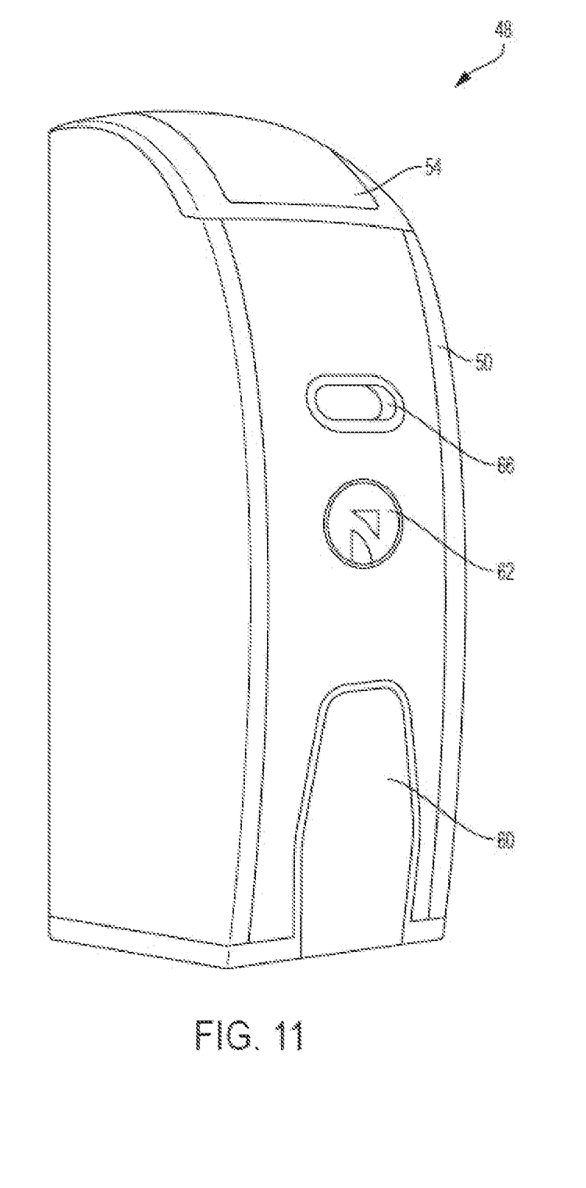
FIG. 11 illustrates an example vaporizer device for vaporizing an inhalable substance according to an exemplary embodiment.
Figure 12:
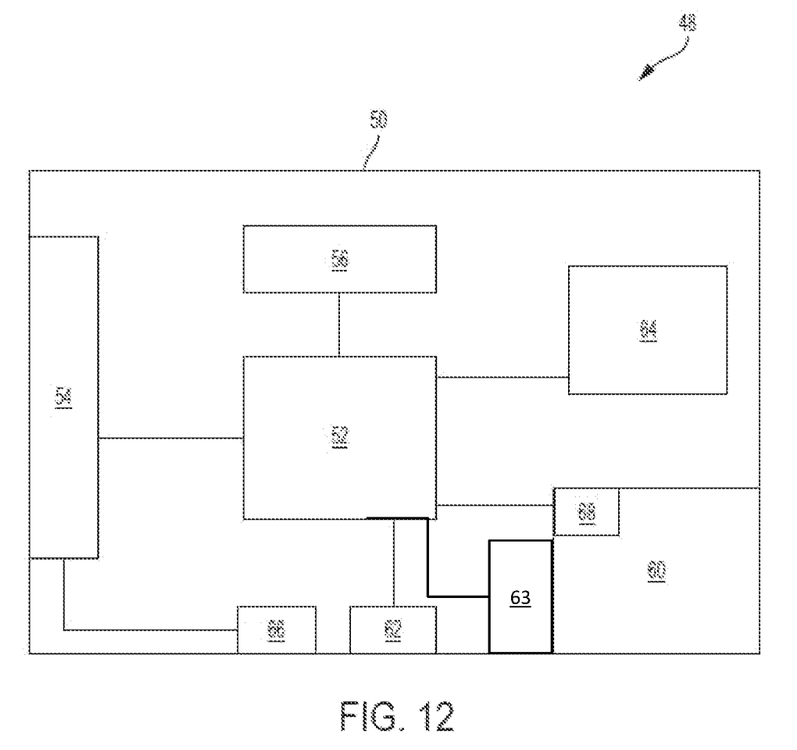
FIG. 12 illustrates a block diagram of an example vaporizer device for vaporizing an inhalable substance according to an exemplary embodiment.

Referring now to FIGS. 11 and 12, an example embodiment of a vaporizer device 48 is shown. According to an exemplary embodiment the vaporizer device 48 comprises a body 50, a processor 52 contained within body 50, computer-readable storage within the body, a mouthpiece 54 formed on the body 50 (e.g. hole), a battery 56, a sealable chamber 60 contained within body 50, a visual indicator 62, a heating unit 63, a haptic indicator 64 within body 50, and a switch or slide 66. Chamber 60 may be configured to open and receive an inhalable substance in either loose form or in cartridges (e.g. prepackaged cartridge 20, prepackaged cartridge 30, user packed cartridge 64, etc.). In one embodiment, chamber 60 may include a micro switch 68 activated when the chamber 60 is opened. The micro switch 68 may act as a reset signal in some embodiments.

In an exemplary embodiment, processor 52 of the vaporizer device 48 is configured to change particular settings of the vaporizer device 48 and convey information through visual indicator 62 and the haptic indicator 64 in response to user input received through mouthpiece 54. The processor 52 may also convey the current state of the various components of the vaporizer device 48 through the visual indicator 62 and/or the haptic indicator 64. In one embodiment, the user input may be a breath intake through mouthpiece 54 measured as a function of airflow through the body 50. In some embodiments, the user input in the form of breath intake may activate the heating unit In one embodiment, processor 52 may be configured to determine the number of breath intakes or air flow "pulls", the speed the pulls though mouthpiece 54, and change the setting of vaporizer 80 in response based on a signal from an airflow sensor or an airflow switch.

Processor 52 may be configured to display a battery status for vaporizer device 48 in response to receiving a predetermined signal such as a predetermined number of breaths (e.g. 3) over a preprogrammed period of time (e.g. in quick succession) through mouthpiece 54. In response, processor 52 may display a particular color on visual indicator 62 to represent a current charge state of battery 56. In one embodiment, processor 52 may distinguish between multiple separate charge states. For example, the multiple separate charge states may be a full, an intermediate, and a low state and may display a different color on visual indicator 62 to represent each state. In an exemplary embodiment, the full state may indicate a battery charge between full and 60%, the intermediate state may indicate a battery charge between 60% and 20%, and the low state may indicate a battery charge below 20%. In an exemplary embodiment, the respective colors for the full, intermediate, and low states may be white, green, and red respectively.

In an exemplary embodiment, processor 52 may activate the vaporizer device 48 from a cold/off state or standby state in response to identifying a predetermined activation signal through mouthpiece 54, such as a single sharp breath intake or any type of breath intake. The processor 52 may determine the sharp breath intake by receiving a high airflow speed measurement from an airflow sensor. In response, processor 52 may blink a first color (e.g. blue) over a periodic interval (e.g. once a second) on visual indicator 62 and engage a heating section of vaporizer 80 or the heating unit to heat the chamber 60 to a first temperature threshold. In an exemplary embodiment, the first temperature threshold may be 180 degrees Celsius. In exemplary embodiments, chamber 60 may reach the first temperature threshold in 22 seconds when starting from a cold state. When chamber 60 reaches the first temperature threshold, processor 52 may change the visual indicator to display a solid steady second color (e.g. cyan) and transmit a first alert signal (e.g. 2 vibrations) using haptic indicator 64. The first alert signal may indicate that the vaporizer is ready to vaporize an inhalable substance.

Following the initial activation of vaporizer 80, processor 52 may raise the temperature of chamber 60 by an incremental amount (e.g. 3 or less degrees Celsius) every time the activation signal is detected (e.g. by detecting airflow by the user) and change the visual indicator 62 to brighter shade of a particular third color (e.g. purple). For example, the second "pull" may be at 181.5 degrees Celsius, the third pull may be at 183 degrees Celsius, and the fourth pull may be 184.5 degrees Celsius. When chamber 60 reaches the new temperature, processor 52 may transmit a second alert signal (e.g. X number of vibrations) using haptic indicator 64. In one embodiment, second alert signal may be the same as the first alert signal. In an exemplary embodiment, processor 52 may continue to raise the temperature by the incremental amount each time the activation signal is detected until a maximum temperature (e.g. 215 degrees Celsius) is reached. When chamber 60 reaches the maximum temperature, the processor 52 may change the visual indicator 62 to a fourth color (e.g. red) and transmit a third alert signal using haptic indicator 64. The transition from the second color to the fourth color may be gradual along the color spectrum. In one embodiment, the third alert signal may comprise 5 rapid vibrations followed by a 15 second pause concluding with 5 more rapid vibrations.

In one embodiment, processor 52 may transition vaporizer 80 into a standby mode if no activation signal has been received within a first predetermined time period (e.g. 30 seconds). When transitioning vaporizer 80 into standby mode, processor 52 may drop the temperature of chamber 60 to a lower standby temperature (e.g. 130 degrees Celsius), and the heating unit may simply keep the chamber 60 warm. In the event that no activation signal is received within a second predetermined time period (e.g. 30 seconds) while vaporizer 80 is in standby mode, processor 52 will transition vaporizer 80 into the off state. In one embodiment, when an activation signal is received following a transition of vaporizer 80 into standby mode or the off state, processor 52 may raise the temperature of chamber 60 to the same temperature level chamber 60 was at prior to transition into standby mode. The computer-readable medium may store the temperature of chamber 60, and the processor will vaporize the inhalable substance at the stored temperature upon reactivation. For example, if the user last inhaled the inhalable substance at 183 degrees Celsius, the processor 52 will store the temperature 184.5 degrees Celsius. The processor 52 will heat the chamber 60 to the stored temperature (here 184.5) whenever the user activates the vaporizer by inhaling through the vaporizer again for the third pull, regardless of the amount of time between pulls.

Processor 52 may reset the temperature setting back to the initial temperature threshold when micro switch 68 associated with chamber 60 is activated (and a door is opened), which indicates opening of chamber 60 to replace the inhalable substance.

Although a few embodiments have been described in detail above, other modifications are possible. For example, the logic flows described above do not require the particular order described, or sequential order, to achieve desirable results. Other steps may be provided, or steps may be eliminated, from the described flows, and other components may be added to, or removed from, the described systems. Other embodiments may be within the scope of the invention.

From the foregoing, it will be observed that numerous variations and modifications may be effected without departing from the spirit and scope of the invention. It is to be understood that no limitation with respect to the specific system or method described herein is intended or should be inferred. It is, of course, intended to cover all such modifications as fall within the sprit and scope of the invention.

What is claimed is:

1. A cartridge comprising:
  an enclosure; and
  an inhalable substance enclosed by the enclosure,
  wherein the enclosure comprises the same combustion properties as the inhalable substance such that a heat from a vaporizer heat source can vaporize the inhalable substance and the enclosure without burning the enclosure,
  wherein the combustion properties comprise a combustion temperature and a vaporization temperature, and
  wherein the heat from the vaporizer heat source is applied at a temperature lower than the combustion temperature of the enclosure such that the heat from the heat source transfers through the enclosure at a substantially similar temperature that does not burn the enclosure.

2. The cartridge of claim 1 wherein the inhalable substance comprises tobacco, marijuana, or atomized medicine.

3. The cartridge of claim 1 wherein the enclosure comprises a biodegradable substance.

4. The cartridge of claim 3 wherein the biodegradable substance comprises hemp paper, hemp cloth, cannabis paper, cannabis cloth, leaf paper, or leaf cloth.

5. The cartridge of claim 1 wherein the enclosure is a wrapper.

6. The cartridge of claim 1 wherein the enclosure comprises a bag and the bag comprises:
  a first tab sealing a first portion of the bag; and
  a second tab sealing a second portion of the bag.

7. The cartridge of claim 1 wherein the enclosure comprises:
  a fillable cartridge having an opening;
  a closure mechanism configured to open and close the opening; and
  a fastener configured to open or seal the closure mechanism.

8. The cartridge of claim 7 wherein the closure mechanism is a drawstring configured to be cinched by the fastener to close the opening.

9. The cartridge of claim 7, wherein the inhalable substance is inserted into the fillable cartridge by a user.

10. An apparatus comprising:
  a vaporizer comprising a chamber and a heating element; and
  a cartridge comprising an enclosure and an inhalable substance,
  wherein the enclosure comprises the same combustion properties as the inhalable sub stance,
  wherein the combustion properties comprise a combustion temperature and a vaporization temperature,
  wherein the chamber receives the cartridge,
  wherein the heating element applies heat to the inhalable substance through the enclosure to vaporize the inhalable substance and the enclosure without burning the enclosure, and
  wherein the heat from the heating element is applied at a temperature lower than the combustion temperature of the enclosure such that the heat from the heat source transfers through the enclosure at a substantially similar temperature that does not burn the enclosure.

11. The apparatus of claim 10 wherein the inhalable substance comprises tobacco, marijuana, or atomized medicine.

12. The apparatus of claim 10 wherein the enclosure comprises a biodegradable substance.

13. The apparatus of claim 12 wherein the biodegradable substance comprises hemp paper, hemp cloth, cannabis paper, cannabis cloth, leaf paper, or leaf cloth.

14. The apparatus of claim 10 wherein the enclosure is a wrapper.

15. The apparatus of claim 10 wherein the enclosure comprises a bag and the bag comprises:
  a first tab sealing a first portion of the bag; and
  a second tab sealing a second portion of the bag.

16. The apparatus of claim 10 wherein the enclosure comprises:
  a fillable cartridge having an opening;
  a closure mechanism configured to open and close the opening; and
  a fastener configured to open or seal the closure mechanism.

17. The apparatus of claim 16 wherein the closure mechanism is a drawstring configured to be cinched by the fastener to close the opening.

18. The apparatus of claim 16 wherein the inhalable substance is inserted into the fillable cartridge by a user.

19. A method comprising:
packing an inhalable substance such that sufficient airflow is achieved when vaporizing the inhalable substance into a gaseous version;
wrapping an enclosure around the inhalable substance to create a cartridge, wherein the enclosure comprises the same combustion properties as the inhalable substance, and wherein the combustion properties comprise a combustion temperature and a vaporization temperature;
inserting the cartridge into a vaporizer; and
applying heat to the enclosure and the inhalable substance of the cartridge at a temperature lower than the combustion temperature of the enclosure to vaporize the inhalable substance and the enclosure without burning the enclosure.

\* \* \* \* \*